United States Patent
Strickler

(10) Patent No.: US 8,092,821 B2
(45) Date of Patent: Jan. 10, 2012

(54) MEDICAL DEVICES HAVING POLYMERIC REGIONS WITH IMPROVED ADHESION

(75) Inventor: Frederick H. Strickler, Natick, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 455 days.

(21) Appl. No.: 11/809,484

(22) Filed: Jun. 1, 2007

(65) Prior Publication Data
US 2008/0051542 A1 Feb. 28, 2008

Related U.S. Application Data

(60) Provisional application No. 60/840,360, filed on Aug. 25, 2006.

(51) Int. Cl.
C08F 212/08 (2006.01)
C08G 77/04 (2006.01)

(52) U.S. Cl. ........ 424/423; 526/273; 526/279; 526/310; 526/313; 526/318.6; 526/347; 526/348.6; 526/348.7; 526/348.8; 528/25

(58) Field of Classification Search .................. None
See application file for complete search history.

(56) References Cited

U.S. PATENT DOCUMENTS

| | | | | |
|---|---|---|---|---|
| 4,829,130 A | 5/1989 | Licchelli et al. | ............... | 525/384 |
| 5,491,193 A | 2/1996 | Erikson | ............ | 525/65 |
| 5,733,925 A | 3/1998 | Kunz et al. | ............... | 514/449 |
| 5,981,785 A | 11/1999 | Faust et al. | ............... | 556/488 |
| 6,051,657 A | 4/2000 | Faust et al. | ............... | 525/284 |
| 6,194,597 B1 | 2/2001 | Faust et al. | ............... | 556/488 |
| 6,306,419 B1 | 10/2001 | Vachon et al. | | |
| 6,469,115 B1 | 10/2002 | Faust et al. | ............... | 526/194 |
| 2002/0107330 A1* | 8/2002 | Pinchuk et al. | ............... | 525/242 |
| 2004/0147999 A1 | 7/2004 | Udipi et al. | ............... | 623/1.11 |
| 2004/0172120 A1 | 9/2004 | Cheng et al. | ............... | 623/1.11 |
| 2004/0236399 A1* | 11/2004 | Sundar | ............... | 623/1.11 |
| 2005/0064011 A1 | 3/2005 | Song et al. | ............... | 424/423 |
| 2006/0013853 A1 | 1/2006 | Richard | ............... | 424/423 |

FOREIGN PATENT DOCUMENTS

| | | | |
|---|---|---|---|
| EP | 1186619 | * | 7/2001 |
| EP | 1493457 | * | 1/2004 |
| EP | 1470830 | * | 4/2004 |
| EP | 1470830 A1 | | 10/2004 |
| EP | 1764118 A2 | | 3/2007 |
| WO | 9704809 A1 | | 2/1997 |
| WO | WO 97/04809 | * | 7/2009 |

OTHER PUBLICATIONS

"Silane Coupling Agents" www.gelest.com/company/pdfs/couplingagents.pdf, exact date unkown but copyright 2006.*
Silane Coupling Agents www.gelest.com/company/pdfs/couplingagents/pdf, exact date unknown, but copyright 2006.*
Richard et al. "Evaluation of Acrylate-Based Block Copolymers Prepared by Atom Transfer Radical Polymerization as Matrices for Paclitaxel Delivery from Coronary Stents" Biomacromolecules 2005, 3410-3418.*
Shen Tang et al., "Enhancement of adhesion strength between two AISI 316 L stainless steel plates through atmospheric pressure plasma treatment," *Surface & Coatings Technology* 200 (2006), pp. 5220-5228.
Laszlo Sipos et al., "Controlled Delivery of Paclitaxel from Stent Coatings Using Poly(hydroxystyrene—b-isobutyleneb-hydroxystyrene) and Its Acetylated Derivative," *Biomacromolecules* 2005, 6, pp. 2570-2582.
H.R. Brown, "Adhesion Between Polymers and Other Substances—A Review of Bonding Mechanisms, Systems and Testing," Source: *Materials Forum*, vol. 24, pp. 49-58, 2000. Downloaded from http://www.azom.com/details.asp?ArticleID=2089 on Mar. 23, 2006.
Gary Alan Nitowski, *Topographic and Surface Chemical Aspects of the Adhesion of Structural Epoxy Resins to Phosphorus Oxo Acid Treated Aluminum Adherends*, Ph.D. Thesis, Virginia Polytechnic Institute and State University, 1998, Chapter 2. Literature Review.
"Silane Coupling Agents," www.gelest.com/company/pdfs/couplingagents.pdf, exact date unknown, but copyright.

* cited by examiner

*Primary Examiner* — Robert A Wax
*Assistant Examiner* — Danah Al-Awadi
(74) *Attorney, Agent, or Firm* — Mayer & Williams PC; David B. Bonham; Keum J. Park

(57) ABSTRACT

According to an aspect of the present invention, implantable or insertable medical devices are provided, which contain at least one polymeric region in contact with a metallic region. The polymeric region contains at least one block copolymer that contains at least one low Tg block and at least one high Tg block. The polymeric region contains at least one polymer that contains at least one adhesion promoting group selected from one or more of halo-silane, alkoxy-silane, epoxy, anhydride, phenoxy, hydroxyl, amino, sulfonate and carboxyl groups, which at least one polymer may correspond to the block copolymer, a supplemental polymer, or both.

22 Claims, 1 Drawing Sheet

MEDICAL DEVICES HAVING POLYMERIC REGIONS WITH IMPROVED ADHESION

STATEMENT OF RELATED APPLICATIONS

This application claims the benefit of U.S. Provisional Patent Application Ser. No. 60/840,360, filed Aug. 25, 2006, entitled "Medical Devices Having Polymeric Regions With Improved Adhesion", which is incorporated by reference herein.

FIELD OF THE INVENTION

The present invention relates generally to medical devices, and more particularly to implantable or insertable medical devices.

BACKGROUND OF THE INVENTION

Thermoplastic elastomers are elastomeric (i.e., reversibly deformable) polymers that form physical crosslinks which are reversible, for example, by dissolving or melting the polymer. Triblock copolymers having an elastomeric low glass transition temperature (Tg) midblock and hard elevated Tg endblocks are common examples of thermoplastic elastomers. As is well known, such copolymers tend to phase separate, with the elastomeric blocks aggregating to form elastomeric phase domains and the hard blocks aggregating to form hard phase domains. Without wishing to be bound by theory, it is believed that because each elastomeric block has a hard block at each end, and because different hard blocks within the same triblock copolymer are capable of occupying two different hard phase domains, the hard phase domains become physically crosslinked to one another via soft blocks.

Examples of such triblock copolymers are poly(styrene-b-isoprene-b-styrene) (SIS), poly(styrene-b-butadiene-b-polystyrene) (SBS), poly(styrene-b-ethylene/butylene-b-styrene) (SEBS), and poly(styrene-b-isobutylene-b-styrene) (SIBS). Taking SIBS as a specific example, these polymers have proven valuable as drug release polymers in implantable or insertable drug-releasing medical devices such as drug-eluting coronary stents. In addition to their drug release characteristics, SIBS copolymers have been shown to have excellent biostability and biocompatibility, particularly within the vasculature. Moreover, they have excellent mechanical properties for coronary stent applications, including good elasticity and high tensile strength. As a result of their mechanical properties, these polymers are able to undergo crimping and to expand as the stent is expanded, for example.

Despite the desirable qualities of these and other thermoplastic elastomers, there are situations where it would be desirable to improve adhesion between these materials and adjacent materials, particularly metallic materials. For example, good adhesion may be desirable where a polymeric coating is located on the outer (abluminal) surface of a metallic stent. Taking SIBS as an example, as seen from FIG. 1, adhesion between SIBS and stainless steel decreases dramatically as one increases the amount of styrene in the SIBS material from 17 mol % styrene to 24.1 mol % styrene. These tests were performed for film compositions containing from 17 to 51 mole % styrene SIBS (sample thickness 0.15-0.21 mm, N=10) utilizing the ASTM D 903-98 peel adhesion method.

SUMMARY OF THE INVENTION

It would be desirable in general to increase adhesion between thermoplastic elastomers and metallic materials.

According to an aspect of the present invention, implantable or insertable medical devices are provided, which contain at least one polymeric region in contact with a metallic region. The polymeric region contains at least one block copolymer that contains at least one low Tg block and at least one high Tg block. The polymeric region contains at least one polymer that contains at least one adhesion promoting group selected from one or more of halo-silane, alkoxy-silane, epoxy, anhydride, carboxyl, phenoxy, hydroxyl, amino and sulfonate groups, which at least one polymer may correspond to the block copolymer, a supplemental polymer, or both.

An advantage of the present invention is that polymeric regions may be provided, which adhere well the metallic regions.

These and other aspects, embodiments and advantages of the present invention will become immediately apparent to those of ordinary skill in the art upon review of the Detailed Description and Claims to follow.

DETAILED DESCRIPTION OF THE INVENTION

Figure 1:
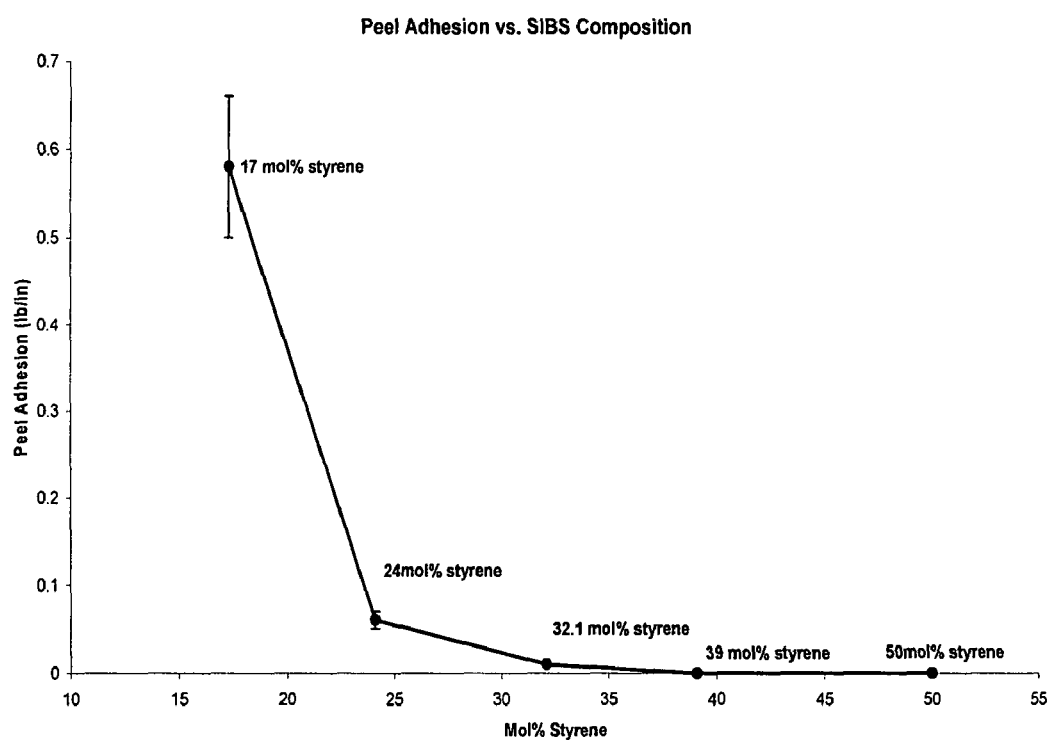
FIG. 1 is a plot of peel adhesion vs. styrene content for SIBS copolymer films containing from 17 to 51 mole % styrene SIBS.

A more complete understanding of the present invention is available by reference to the following detailed description of numerous aspects and embodiments of the invention. The detailed description of the invention which follows is intended to illustrate but not limit the invention.

According to an aspect of the present invention, implantable or insertable medical devices are provided, which contain at least one polymeric region in contact with a metallic region. The polymeric region contains at least one block copolymer that includes at least one low Tg block and at least one high Tg block. The polymeric region contains at least one polymer that includes at least one adhesion promoting group selected from one or more of halo-silane, alkoxy-silane, epoxy, anhydride, phenoxy, hydroxyl, amino, sulfonate and carboxyl groups, which at least one polymer may correspond to the block copolymer, a supplemental polymer, or both.

Medical devices benefiting from the present invention vary widely and include medical devices that are implanted or inserted into a subject, either for procedural uses or as implants.

Examples of medical devices include, for example, catheters (e.g., renal or vascular catheters such as balloon catheters and various central venous catheters), guide wires, balloons, filters (e.g., vena cava filters and mesh filters for distil protection devices), stents (including coronary vascular stents, peripheral vascular stents, cerebral, urethral, ureteral, biliary, tracheal, gastrointestinal and esophageal stents), stent grafts, vascular grafts, abdominal aortic aneurysm (AAA) devices such as AAA stents and AAA grafts, vascular access ports, dialysis ports, embolization devices including cerebral aneurysm filler coils (including Guglilmi detachable coils and metal coils), embolic agents, septal defect closure devices, myocardial plugs, patches, pacemakers, lead coatings including coatings for pacemaker leads, defibrillation leads and coils, ventricular assist devices including left ventricular assist hearts and pumps, total artificial hearts, shunts, valves including heart valves and vascular valves, anastomosis clips and rings, suture anchors, tissue staples and ligating clips at surgical sites, cannulae, metal wire ligatures, urethral slings, hernia "meshes", artificial ligaments, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair, and dental devices such as dental implants, cochlear implants, tissue bulking devices, and tissue engineering scaffolds for cartilage, bone, skin and other in vivo tissue regeneration, biopsy devices, and any coated metallic substrate that is implanted or inserted into the body.

Medical devices benefiting from the present invention thus include a variety of implantable and insertable medical devices including devices for insertion into and/or through a wide range of body lumens, including lumens of the cardiovascular system such as the heart, arteries (e.g., coronary, femoral, aorta, iliac, carotid and vertebro-basilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract such as the trachea, bronchi, nasal passages and sinuses, lumens of the gastrointestinal tract such as the esophagus, gut, duodenum, small intestine, large intestine, rectum, biliary and pancreatic duct systems, lumens of the lymphatic system, the major body cavities (peritoneal, pleural, pericardial) and so forth.

In certain embodiments, the polymeric regions are in the form of polymeric layers covering all or only a portion of an underlying metallic substrate. As used herein a "layer" of a given material is a region of that material whose thickness is small compared to both its length and width. As used herein a layer need not be planar, for example, taking on the contours of an underlying substrate. Layers can be discontinuous (e.g., patterned).

For example, the medical device may be a stent (e.g., a cardiovascular stent) in which (a) the entire stent is covered with a polymeric layer in accordance with the invention or (b) only the inner surface of the stent or only the outer surface of the stent is provided with a polymeric layer in accordance with the invention (e.g., it is desirable in some embodiments to provide a polymeric layer that releases an anti-restenotic agent on an outer surface of the stent, while leaving the inner surface bare). Loss of adhesion in situation (b) is particularly problematic as it can result in complete detachment of the polymer layer from the device.

In certain embodiments, one or more therapeutic agents are provided on or within the polymeric regions in accordance with the invention.

As used herein, a "metallic region" is a region (e.g., an entire device, a device component, a device coating layer, etc.) that contains metals, for example, from 50 wt % or less to 75 wt % to 90 wt % to 95 wt % to 97.5 wt % to 99 wt % or more metals.

Metallic regions include, pure or substantially pure metals (e.g., biostable metals such as gold, platinum, palladium, iridium, osmium, rhodium, titanium, tantalum, tungsten, and ruthenium, and bioabsorbable metals such as magnesium and iron) and metal alloys, including alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys), and bioabsorbable metal alloy such as magnesium alloys and iron alloys, including their alloys with various combinations of Ce, Ca, Zn, Zr and Li.

As used herein, a "polymeric region" is a region that contains polymers, for example, from 50 wt % or less to 75 wt % to 90 wt % to 95 wt % to 97.5 wt % to 99 wt % or more polymers.

As used herein, "polymers" are molecules containing multiple copies (e.g., from 2 to 5 to 10 to 25 to 50 to 100 to 250 to 500 to 1000 or more copies) of one or more constitutional units, commonly referred to as monomers.

Polymers may take on a number of configurations, which may be selected, for example, from cyclic, linear and branched configurations, among others. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ in composition, for instance, because a constitutional unit (i.e., a monomer) is found in one polymer block that is not found in another polymer block. As used herein, a "polymer block" is a grouping of constitutional units (e.g., 2 to 5 to 10 to 25 to 50 to 100 to 250 to 500 to 1000 or more units). Blocks can be branched or unbranched. Blocks can contain a single type of constitutional unit (also referred to herein as "homopolymeric blocks") or multiple types of constitutional units (also referred to herein as "copolymeric blocks") which may be present, for example, in a random, statistical, gradient, or periodic (e.g., alternating) distribution.

As used herein a "chain" is a linear polymer or a portion thereof, for example, a linear block.

As used herein, a "low Tg polymer block" is one that displays a Tg that is below body temperature, more typically from 35° C. to 20° C. to 0° C. to −25° C. to −50° C. or below. Conversely, as used herein, an elevated or "high Tg polymer block" is one that displays a Tg that is above body temperature, more typically from 40° C. to 50° C. to 75° C. to 100° C. or above. Tg can be measured by differential scanning calorimetry (DSC).

Specific examples of low Tg polymer blocks include homopolymer and copolymer blocks containing one or more of the following (listed along with published Tg's for homopolymers of the same): (1) alkene monomers including ethylene, propylene (Tg −8 to −13° C.), isobutylene (Tg −73° C.), 1-butene (Tg −24° C.), 4-methyl pentene (Tg 29° C.), 1-octene (Tg −63° C.) and other α-olefins, dienes such as 1,3-butadiene, 2-methyl-1,3-butadiene(isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, and 3-butyl-1,3-octadiene; (2) acrylic monomers including: (a) alkyl acrylates such as methyl acrylate (Tg 10° C.), ethyl acrylate (Tg −24° C.), propyl acrylate, isopropyl acrylate (Tg −11° C., isotactic), butyl acrylate (Tg −54° C.), sec-butyl acrylate (Tg −26° C.), isobutyl acrylate (Tg −24° C.), cyclohexyl acrylate (Tg 19° C.), 2-ethylhexyl acrylate (Tg −50° C.), dodecyl acrylate (Tg −3° C.) and hexadecyl acrylate (Tg 35° C.), (b) arylalkyl acrylates such as benzyl acrylate (Tg 6° C.), (c) alkoxyalkyl acrylates such as 2-ethoxyethyl acrylate (Tg −50° C.) and 2-methoxyethyl acrylate (Tg −50° C.), (d) halo-alkyl acrylates such as 2,2,2-trifluoroethyl acrylate (Tg −10° C.) and (e) cyano-alkyl acrylates such as 2-cyanoethyl acrylate (Tg 4° C.); (3) methacrylic monomers including (a) alkyl methacrylates such as butyl methacrylate (Tg 20° C.), hexyl methacrylate (Tg −5° C.), 2-ethylhexyl methacrylate (Tg −10° C.), octyl methacrylate (Tg −20° C.), dodecyl methacrylate (Tg −65° C.), hexadecyl methacrylate (Tg 15° C.) and octadecyl methacrylate (Tg −100° C.) and (b) aminoalkyl methacrylates such as diethylaminoethyl methacrylate (Tg 20° C.) and 2-tert-butyl-aminoethyl methacrylate (Tg 33° C.); (4) vinyl ether monomers including (a) alkyl vinyl ethers such as ethyl vinyl ether (Tg −43° C.), propyl vinyl ether (Tg −49° C.), butyl vinyl ether (Tg −55° C.), isobutyl vinyl ether (Tg −19° C.), 2-ethylhexyl vinyl ether (Tg −66° C.) and dodecyl vinyl ether (Tg −62° C.); (5) cyclic ether monomers include tetrahydrofuran (Tg −84° C.), trimethylene oxide (Tg −78° C.), ethylene oxide (Tg −66° C.), propylene oxide (Tg −75° C.), methyl glycidyl ether (Tg −62° C.), butyl glycidyl ether (Tg −79° C.), allyl glycidyl ether (Tg −78° C.), epibromohydrin (Tg −14° C.), epichlorohydrin (Tg −22° C.), 1,2-epoxybutane (Tg −70° C.), 1,2-epoxyoctane (Tg −67° C.) and 1,2-epoxydecane (Tg −70° C.); (6) ester monomers (other than the above acrylates and methacrylates) including ethylene malonate (Tg −29° C.), vinyl acetate (Tg 30° C.), and vinyl propionate (Tg 10° C.); (7) halogenated alkene monomers including vinylidene chloride (Tg −18° C.), vinylidene fluoride (Tg −40° C.), cis-chlorobutadiene (Tg −20° C.), and trans-chlorobutadiene (Tg −40° C.); and (8) siloxane monomers including dimethylsiloxane (Tg −127° C.), diethylsiloxane, methylethylsiloxane, methylphenylsiloxane (Tg −86° C.), and diphenylsiloxane.

Specific examples of high Tg polymer blocks include homopolymer and copolymer blocks containing one or more of the following: (1) vinyl aromatic monomers including (a) unsubstituted vinyl aromatics, such as styrene (Tg 100° C.) and 2-vinyl naphthalene (Tg 151° C.), (b) vinyl substituted aromatics such as alpha-methyl styrene, and (c) ring-substituted vinyl aromatics including ring-alkylated vinyl aromatics such as 3-methylstyrene (Tg 97° C.), 4-methylstyrene (Tg 97° C.), 2,4-dimethylstyrene (Tg 112° C.), 2,5-dimethylstyrene (Tg 143° C.), 3,5-dimethylstyrene (Tg 104° C.), 2,4,6-trimethylstyrene (Tg 162° C.), and 4-tert-butylstyrene (Tg 127° C.), ring-alkoxylated vinyl aromatics, such as 4-methoxystyrene (Tg 113° C.) and 4-ethoxystyrene (Tg 86° C.), ring-halogenated vinyl aromatics such as 2-chlorostyrene (Tg 119° C.), 3-chlorostyrene (Tg 90° C.), 4-chlorostyrene (Tg 110° C.), 2,6-dichlorostyrene (Tg 167° C.), 4-bromostyrene (Tg 118° C.) and 4-fluorostyrene (Tg 95° C.), and ring-ester-substituted vinyl aromatics such as 4-acetoxystyrene (Tg 116° C.); (2) other vinyl monomers including (a) vinyl esters such as vinyl benzoate (Tg 71° C.), vinyl 4-tert-butyl benzoate (Tg 101° C.), vinyl cyclohexanoate (Tg 76° C.), vinyl pivalate (Tg 86° C.), vinyl trifluoroacetate (Tg 46° C.), vinyl butyral (Tg 49° C.), (b) vinyl amines such as 2-vinyl pyridine (Tg 104° C.), 4-vinyl pyridine (Tg 142° C.), and vinyl carbazole (Tg 227° C.), (c) vinyl halides such as vinyl chloride (Tg 81° C.) and vinyl fluoride (Tg 40° C.); (d) alkyl vinyl ethers such as tert-butyl vinyl ether (Tg 88° C.) and cyclohexyl vinyl ether (Tg 81° C.), and (e) other vinyl compounds such as vinyl ferrocene (Tg 189° C.); (3) other aromatic monomers including acenaphthalene (Tg 214° C.) and indene (Tg 85° C.); (4) methacrylic monomers including (a) methacrylic acid anhydride (Tg 159° C.), (b) methacrylic acid esters (methacrylates) including (i) alkyl methacrylates such as methyl methacrylate (Tg 105-120° C.), ethyl methacrylate (Tg 65° C.), isopropyl methacrylate (Tg 81° C.), isobutyl methacrylate (Tg 53° C.), t-butyl methacrylate (Tg 118° C.) and cyclohexyl methacrylate (Tg 92° C.), (ii) aromatic methacrylates such as phenyl methacrylate (Tg 110° C.) and including aromatic alkyl methacrylates such as benzyl methacrylate (Tg 54° C.), (iii) hydroxyalkyl methacrylates such as 2-hydroxyethyl methacrylate (Tg 57° C.) and 2-hydroxypropyl methacrylate (Tg 76° C.), (iv) additional methacrylates including isobornyl methacrylate (Tg 110° C.) and trimethylsilyl methacrylate (Tg 68° C.), and (c) other methacrylic-acid derivatives including methacrylonitrile (Tg 120° C.); (5) acrylic monomers including (a) certain acrylic acid esters such as tert-butyl acrylate (Tg 43-107° C.), hexyl acrylate (Tg 57° C.) and isobornyl acrylate (Tg 94° C.); and (b) other acrylic-acid derivatives including acrylonitrile (Tg 125° C.).

As used herein, a poly(vinyl aromatic) block is a block that contains multiple copies of one or more types of vinyl aromatic monomers, a polyalkene block is a block that contains multiple copies of one or more types of alkene monomers, and so forth.

Block copolymer configurations may vary widely and include, for example, the following configurations, among others, which comprise two more high Tg polymer chains (designated "H") and one or more low Tg polymer chains (designated "L"),: (a) block copolymers having alternating chains of the type HLH, $(HL)_m$, $L(HL)_m$ and $H(LH)_m$ where m is a positive whole number of 2 or more, (b) multiarm copolymers such as $X(LH)_n$, where n is a positive whole number of 2 or more, and X is a hub species (e.g., an initiator molecule residue, a linking residue, etc.), and (c) comb copolymers having an L chain backbone and multiple H side chains.

In certain embodiments poly(vinyl aromatic-b-alkene-b-vinyl aromatic) copolymers such as SIBS are employed, which contain more than 18 mol % vinyl aromatic monomer, for example, from 18 to 20 to 22 to 25 to 30 to 35 mol % vinyl aromatic monomer or more.

As noted above, the medical devices of the present invention contain at least one polymeric region disposed on a metallic region. The polymeric region contains at least one block copolymer that contains at least one low Tg block and at least one high Tg block.

The polymeric region contains at least one polymer that contains at least one adhesion promoting group selected from one or more of halo-silane, alkoxy-silane, epoxy, anhydride, phenoxy, hydroxyl, amino, sulfonate and carboxyl groups, which at least one polymer may correspond to the block copolymer, a supplemental polymer, or both. An advantage of polymers having these groups is that adhesion between polymeric regions containing such polymers and an underlying metallic region may be improved, for example, through the formation of covalent bonds between the polymers and the metallic regions, by the formation of hydrogen bonds between the polymers and the metallic regions, and so forth.

Thus, in some embodiments, a block copolymer is provided which has at least one adhesion promoting group selected from one or more of halo-silane, alkoxy-silane, epoxy, anhydride, phenoxy, hydroxyl, amino, sulfonate and carboxyl groups. In other embodiments, a block copolymer is blended with a supplemental polymer that has at least one adhesion promoting group selected from one or more of halo-silane, alkoxy-silane, epoxy, anhydride, phenoxy, hydroxyl, amino, sulfonate and carboxyl groups. The block copolymers and/or supplemental polymers may be provided with such groups either during or subsequent to polymerization of the same. Such groups may be provided at one or more chain ends of the polymers, within the backbone(s) of the polymers, or a combination of both.

In embodiments where the block copolymer and/or a supplemental polymer comprises one or more halo- or alkoxy-silane groups (e.g. one or more —$SiY_nR_{3-n}$ groups, where R is independently selected from alkyl groups having 1 to 10 carbon atoms and aryl groups having from 6 to 10 carbon atoms, where Y is independently halogen or —OR', where R' is independently selected from alkyl groups having 1 to 10 carbon atoms, and where n is 1, 2 or 3), reaction may proceed upon exposure to water, which causes the halo-silane or alkoxy-silane groups in the polymer to be hydrolyzed into hydroxy-silane groups, followed by condensation reactions (a) between the hydroxy-silane groups and the hydroxyl (—OH) groups which are commonly found on metallic surfaces, thereby forming M-O—Si— linkages, where M represents a metal atom at the metallic surface and/or (b) between neighboring hydroxy-silane groups, thereby forming —Si—O—Si— linkages. These processes may be promoted, for example, by heating, steam autoclaving or through the use of a suitable catalyst.

The formation of metal oxides and hydroxyl groups at the metallic surface may be promoted, for example, by plasma treatment. In this regard, see, e.g., S. Tang et al., "Enhancement of adhesion strength between two AISI 316 L stainless steel plates through atmospheric pressure plasma treatment," *Surface & Coatings Technology* 200 (2006) 5220-5228.

Where each polymer contains one Y group available for hydrolysis, the polymer can bond, for example, to the metal surface or to another polymer molecule that contains a Y group. Where each polymer contains two or more Y groups, then polymer can bond, for example, to the metal surface, to itself, to another polymer that contains a Y group, or to a combination thereof.

Where silane-containing polymers are not available commercially, they may be formed using various known techniques. For example, silane compounds that have a combination of unsaturated and hydrolyzable groups may be grafted, for instance, onto polyalkenes (e.g., polymers containing ethylene and/or butylene) under free radical generating conditions (e.g., in the presence of a suitable peroxide catalyst or in the presence of ionizing radiation). As a specific example, vinyl trimethoxysilane has been grafted to polyethylene using dicumyl peroxide as the grafting agent.

Using analogous processes, in accordance with the invention, block copolymers with polymer blocks containing, for example, ethylene, propylene or both, may be reacted with species having one or more sites of unsaturation and one or more hydrolysable silane groups. Specific examples of such silanes, among others, include species of the formula HC=CH—$(CH_2)_n$—Si—$(OR)_3$, where n is an integer, for example, ranging from 0 to 20, and R is selected from alkyl groups having 1 to 10 carbon atoms. Specific examples of such block copolymers include polyalkene block copolymers (e.g., triblock copolymers having high Tg endblocks and having low Tg centerblocks that contain ethylene, propylene or both, etc.). Commercially available examples of block copolymers of this type include, for instance, KRATON G series polymers from Kraton Polymers, Houston Tex., USA, specifically SEBS, a poly(styrene-b-ethylene/butylene-b-styrene) triblock copolymer (e.g., KRATON G 1650, 1651, 1652, 1654, 1657, etc.).

It is also known to graft unsaturated acid anhydrides onto polymer chains, including those containing ethylene or propylene. For instance, it is known to graft of maleic anhydride onto polyalkene chains in the presence of organic peroxides. Maleation of polyalkene chains may be performed, for example, in solution or in the melt phase (e.g., by reactive extrusion, etc.), among other processes. Using analogous processes, block copolymers containing ethylene, propylene or both, may be maleated. Block copolymers of this type are commercially available. For example, maleated SEBS is available from Kraton Polymers as Kraton FG series polymers (e.g., FG1901 or FG1924X).

It is also possible to functionalize the metal surface with various functional groups which can react with polymers containing functional groups. Hydroxyl, carboxylate, amino, and anhydride functional silanes are available from Gelest, Inc., Morrisville, Pa., USA. According to the Gelest catalog, the functionalized silane (coupling agent) can be combined with a dipodal material, such as, bis(triethoxysilyl) ethane at a 1:5 to 1:10 ratio with the coupling agent. The dipodal agents impact (increase) bonding to the metal substrate.

Anhydrides are known to react with hydroxyl groups, including those formed on metallic surfaces. Anhydride units (including residual anhydride units remaining subsequent to reaction with surface hydroxyl atoms) are also known to undergo ring opening in the presence of moisture, thereby generating carboxylic acid groups. These groups may, for example, interact by coordination complexation to the metal surface, or they may, for example, react with hydroxyl-functionalized surfaces (e.g., those formed by reaction with a carboxylate functionalized silane) forming ester type bonds (e.g., M-O—CO—C bonds) (if needed, a catalyst such as HCl or another suitable catalyst may be employed), or they may, for example, form hydrogen bonds with oxygen atoms and hydroxyl groups at the metal surface, increasing adhesion via this mechanism as well.

In other embodiments, dienes are reacted with peroxy acids to form epoxy groups, which can form hydrogen bonds with hydroxyl groups at the metallic surface or which can be reacted with acids, amines, and/or anhydrides to form covalent bonds. In this connection, acids, amines, and/or anhydrides are commonly used to crosslink epoxy resins. If desired, the dienes may be partially hydrogenated prior to formation of epoxy groups, as described in U.S. Pat. No. 5,491,193 to Erickson. For example, in Erickson, polymers are hydrogenated to produce a partially hydrogenated polymer which has remaining about 0.1 to about 5 milliequivalents per gram of polymer of residual aliphatic double bonds. The partially hydrogenated polymer is contacted with a peroxy acid to form an epoxidized polymer, which has between 0.1 and about 5 milliequivalents of epoxide per gram of polymer.

Other embodiments of the invention involve the incorporation of reactive species in conjunction with polymerization processes. For example, block copolymers may be rendered more reactive by providing reactive groups at one or more chain ends, within one or more chains, or a combination thereof, either during or after the polymerization process.

In this regard, cationic polymerization of unsaturated monomers, including alkenes such as isobutylene, butadiene, isoprene, methylbutene, and 2-methylpentene, among others, or vinyl aromatic monomers, such as styrene, p-methylstyrene, alpha-methylstyrene and indene, among others, is well known. In a typical cationic polymerization process a suitable unsaturated monomer is polymerized in the presence of a cationic polymerization catalyst, an initiator, and an optional Lewis base (in order to prevent initiation by protic impurities), generally in an aprotic solvent under dry conditions at low temperature. The polymers formed in this method are living cationic polymers (e.g., polymers in which the polymer chains typically continue to grow from the site of initiation until the monomer supply is exhausted, rather than terminating when the chain reaches a certain length or when the catalyst is exhausted). The cationic polymerization catalyst may be, for example, a Lewis acid (e.g., $BCl_3$ or $TiCl_4$, among others). The initiator may be, for example, an alkyl halide or (haloalkyl)-aryl compound, for example, a monofunctional initiator such as 2-chloro-2,4,4-trimethylpentane, a bifunctional initiator such as 1,3-di(1-chloro-1-methylethyl)-5-(t-butyl)benzene, or a trifunctional initiator such as 1,3,5-tri(1-chloro-1-methylethyl)benzene, among others. Lewis bases include pyridine and its derivatives, such as 2,6-ditert-butylpyridine (DTBP) or lutidine, among others.

In a specific example, a cationically polymerizable alkene such as isobutylene may be polymerized in the presence of a bifunctional initiator (e.g., 1,3-di(1-chloro-1-methylethyl)-5-(t-butyl)benzene, among others) followed by continued polymerization of a cationically polymerizable vinyl aromatic monomer such as styrene from the two polyalkene chain ends, thereby forming a poly(vinyl aromatic-b-alkene-b-vinyl aromatic) triblock copolymer (the presence of the initiator residue is typically ignored in block copolymer terminology as it is a minor component of the copolymer).

To render a poly(vinyl aromatic-b-alkene-b-vinyl aromatic) copolymer such as SIBS more reactive, a small amount of a diene, for instance, isoprene or butadiene, may be added during the cationic polymerization process (e.g., admixed with the isobutylene or added prior and/or subsequent to the isobutylene), thereby yielding SIBS having unsaturation within the polyisobutylene blocks or at the ends thereof. Such a polymer can then be modified, for example, using techniques such as those described above. For example, the polymer may undergo chemical reaction to create adhesion promoting groups (e.g., alkoxysilane groups, anhydride groups, epoxy groups, etc.) within the polymer backbone as described above.

In certain embodiments of the invention, reactive functional groups (e.g., hydroxyl groups) are incorporated into the polymer using protective groups. For example, a poly(hydroxystyrene-b-isobutylene-b-hydroxystyrene) polymer has previously been synthesized using protective groups. See L. Sipos et al., "Controlled Delivery of Paclitaxel from Stent Coatings Using Poly(hydroxystyrene-b-isobutylene-b-hydroxystyrene) and Its Acetylated Derivative," *Biomacromolecules* 2005, 6, 2570-2582. The metal surface can be functionalized by reacting carboxylate or anhydride functionalized silanes. The hydroxyl group itself will coordinate with the metal oxides and hydroxyl groups on the surface.

U.S. Pat. Nos. 5,981,895, 6,051,657 and 6,194,597, each to Faust et al. and hereby incorporated by reference, describe methods for preparing silyl-functional living cationic polymers which can be coupled to one another to form a moisture-curable telechelic system. The methods utilize a functional initiator for the polymerization process, followed by a coupling the chain ends together using a difunctional linking agent to form a moisture curable polymer. More particularly, the methods described comprise reacting, in the presence of a Lewis acid, at least one cationically polymerizable monomer with a functional initiator which comprises a typical cationic polymerization initiation group (e.g., a halogen, alkoxy, acyloxy or hydroxyl group) and a silane group (e.g., $-SiX_nR_{3-n}$, wherein R is selected from alkyl groups having 1 to 10 carbon atoms or aryl groups having 6 to 10 carbon atoms, X is halogen, and n is 1, 2 or 3), for instance,

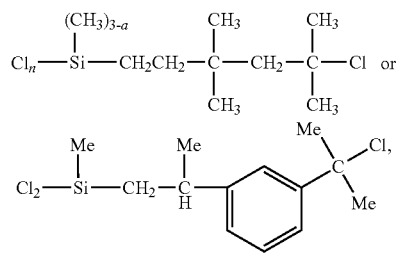

among others. The resulting living polymer is then coupled using a suitable coupling agent, for example, a molecule having at least two furan rings, for instance,

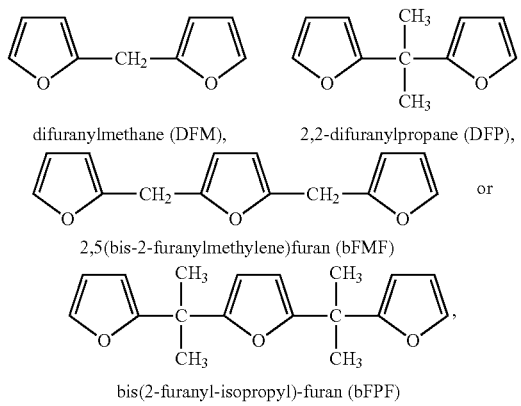

among others.

According to one embodiment, copolymers for use in the present invention may be prepared, for example, by polymerization of a first cationically polymerizable high Tg monomer (e.g., a vinyl aromatic monomers such as styrene) from a silyl functional initiator, followed by polymerization of a second low Tg monomer (e.g., an alkene such as isobutylene). The resulting silyl functionalized diblock copolymer may then be coupled to itself with a suitable coupling agent, for example, a molecule having at least two furan rings such as those described above, among others. The resulting HLH triblock copolymer (this terminology ignores the presence of the initiator and coupling group residues, as noted above) is then reacted with an alcohol (e.g., methanol, ethanol, propanol, butanol, etc.), whereby the halogen groups on silicon atoms are replaced by an alkoxy functionality that corresponds to the alcohol. The resulting alkoxysilyl-functional polymer may then be isolated from the reaction solution by conventional means, such as precipitation with a non-solvent.

Such polymers may be reacted with hydroxyl groups at the metal surface, with themselves, or with other polymers (where the other polymers contain one or more alkoxysilyl groups), and they may optionally contain additional agents such as catalysts to promote the reaction, solvents, therapeutic agents, and so forth.

As another specific example, a difunctional initiator may be employed, with low Tg monomer polymerization proceeding before high Tg monomer polymerization. Then, a silyl-functional vinyl aromatic monomer such as one of those described in U.S. Pat. No. 6,469,115 to Faust et al., which is hereby incorporated by reference, is added, thereby producing a SIBS block copolymer with silyl-vinyl-aromatic groups at the chain ends. Examples of silyl-functional vinyl aromatic monomers include, for example,

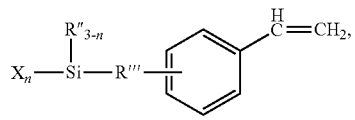

where R" is independently selected from alkyl groups having 1 to 10 carbon atoms or aryl groups having 6 to 10 carbon atoms, R'" is a divalent non-aromatic hydrocarbon group having 2 to 6 carbon atoms, X is a halogen group, and n is independently 1, 2 or 3, for example, 2-dichlorolmethylsilyl-ethyl-styrene (DSiSt).

Such polymers may be reacted with an alcohol, isolated, and reacted with hydroxyl groups at the metal surface (and/or reacted with themselves or other silyl-group containing polymers), and they may optionally contain additional agents such as catalysts to promote the reaction, solvents, therapeutic agents, and so forth.

The groups themselves can coordinate with the metal oxides and hydroxyl groups on the metallic surface. Amines can react with anhydrides to form an amide. Phenoxides can react with anhydrides and alkyl halides to form ethers (although a base catalyst is typically needed).

In certain embodiments of the invention, an interpenetrating polymer network (IPN) or a semi-IPN is created in which a supplemental polymer that contains at least one adhesion promoting group, selected from one or more of halo-silane, alkoxy-silane, epoxy, anhydride, phenoxy, hydroxyl, amino, sulfonate and carboxyl groups, is adhered to the surface in the presence of a block copolymer that contains (a) at least one low Tg block and (b) at least one high Tg block. Without wishing to be bound by theory, it is believed that upon adhering the supplemental polymer to the metallic region, the block copolymer is adhered as well through chain entanglement or another mechanism.

Examples of supplemental polymers include those that covalently react with metallic surfaces and/or those that adhere to metallic surfaces via other mechanisms such as hydrogen bonding. Specific examples of such polymers include homopolymer and copolymers that contain monomer units that match or are similar to the monomer units of the block copolymer. For example, wherein a polyalkene-poly (vinyl aromatic) block copolymer is employed, specific examples of supplemental polymers include homopolymers and copolymers that contain alkene units, for example, olefin units such as ethylene and/and propylene units, or diene units such as isoprene and/or butadiene units, among others. As noted above, such polymers may undergo chemical reaction to create adhesion promoting groups along the polymer backbone (e.g., alkoxysilane groups, anhydride groups, epoxy groups, carboxyl groups, phenoxy groups, hydroxyl groups, amino groups, sulfonate groups, etc.). Further specific examples include polymers which are formed using functional initiators, functional monomers and/or functional endcaps (e.g., silyl functional initiators, monomers, and/or endcaps, among others), as well as protected forms of the same. Additional information regarding these specific examples is discussed above, and is applicable to homopolymers and copolymers other than the block copolymers exemplified.

For example, a supplemental polymer, for instance, a homopolymer such as polyethylene, polybutylene, polyisobutylene, polystyrene, or a copolymer thereof may be provided which contains groups (e.g., alkoxysilane groups, epoxy groups, anhydride groups, carboxyl groups, phenoxy groups, hydroxyl groups, amino groups, sulfonate groups, etc.) that adhere to species found at metallic surfaces (e.g., metal oxides and metal hydroxides), which supplemental polymer may be adhered to such a metallic surface in the presence of (a) a triblock copolymer having a reactive low Tg midblock and high Tg endblocks, for example, the SEBS copolymer, or (b) a triblock copolymer having a nonreactive low Tg midblock and high Tg endblocks, for example, the SIBS copolymer. As above, the reaction may optionally proceed in the presence of catalysts.

As noted above, in certain embodiments, one or more therapeutic agents are provided on or within the polymeric regions in accordance with the invention. "Therapeutic agents", "drugs", "pharmaceutically active agents", "pharmaceutically active materials", and other related terms may be used interchangeably herein.

Exemplary therapeutic agents for use in conjunction with the present invention include the following: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anticoagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in conjunction with the medical devices of the present invention, with the therapeutically effective amount being readily determined by those of ordinary skill in the art. Typical loadings range, for example, from 1 wt % or less to 2 wt % to 5 wt % to 10 wt % to 25 wt % or more of the polymeric region.

Medical devices having sustained release profiles are beneficial in certain embodiments of the invention. By "sustained release profile" is meant a release profile in which effective amounts of therapeutic agents are released from the medical device to the host tissue or physiological environment over an extended period, such as days, weeks or even months.

Numerous techniques are available for forming polymeric regions in accordance with the present invention.

For example, where the polymeric region is formed from one or more polymers having thermoplastic characteristics, a variety of standard thermoplastic processing techniques may be used to form the polymeric region. Using these techniques, a polymeric region can be formed by (a) first contacting a melt, which contains the polymer(s) and any supplemental agents such as catalyst(s), therapeutic agent(s), and so forth, with a metallic surface and (b) subsequently cooling the melt.

Other processing techniques besides thermoplastic processing techniques may also be used to form the polymeric regions of the present invention, including solvent-based techniques. Using these techniques, a polymeric region can be formed by (a) first providing a solution or dispersion that contains the polymer(s) and any supplemental agents such as catalyst(s), therapeutic agent(s), and so forth and (b) subsequently removing the solvent. The solvent that is ultimately selected will contain one or more solvent species, which are generally selected based on their ability to dissolve the polymer(s) that form the polymeric region (and in many embodiments, the therapeutic agent(s) and supplemental agent(s), if any, as well), in addition to other factors, including drying rate, surface tension, etc.

In some embodiments of the invention, a polymer containing solution (where solvent-based processing is employed) or a polymer melt (where thermoplastic processing is employed) is applied to a substrate to form a polymeric region. For example, the substrate can correspond to all or a portion of an implantable or insertable medical device to which a polymeric coating is applied. Application techniques include spin coating techniques, web coating techniques, spraying techniques, dipping techniques, techniques involving coating via mechanical suspension including air suspension, ink jet techniques, electrostatic application techniques, and combinations of these processes, among others.

Reaction may be induced, for example, during or subsequent to such processes, for example, by exposure to energy (e.g., heat, etc.), to a chemical species (e.g., moisture), or to any other agent that results in reaction.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising a polymeric region in the form of a single layer in contact with a metallic region, said polymeric region comprising a block copolymer that comprises a low Tg block and a high Tg block, said block copolymer comprising an adhesion promoting group selected from halo-silane groups, alkoxy-silane groups, epoxy groups, anhydride groups, and combinations thereof, wherein said block polymer is covalently bound to said metallic region through said adhesion promoting group, and wherein said medical device is an implantable or insertable medical device.

2. The medical device of claim 1, comprising a plurality of polymeric regions.

3. The medical device of claim 1, wherein said block copolymer is a multiarm block copolymer comprising a low Tg midblock and a plurality of high Tg end blocks.

4. The medical device of claim 3, wherein said low Tg midblock is selected from polyolefin, polyacrylate and polysiloxane blocks and wherein said high Tg endblocks are selected from poly(vinyl aromatic) and polymethacrylate blocks.

5. The medical device of claim 3, wherein said low Tg midblock is a polyalkene block and said high Tg endblocks are poly(vinyl aromatic) blocks.

6. The medical device of claim 5, wherein said polyalkene block comprises a monomer selected from ethylene, butylene, isobutylene, butadiene, isoprene, and combinations of the same.

7. The medical device of claim 5, wherein said polyvinyl aromatic blocks comprise an aromatic monomer selected from styrene, alkyl substituted styrenes, and combinations of the same.

8. The medical device of claim 1, wherein said adhesion promoting group is an epoxy group.

9. The medical device of claim 1, wherein said adhesion promoting group is an anhydride group.

10. The medical device of claim 1, wherein said adhesion promoting group is selected from halo-silane groups, alkoxy-silane groups, and combinations thereof.

11. The medical device of claim 1, wherein said polymeric region further comprises an additional polymer that comprises a monomer unit that matches a monomer unit of said block copolymer.

12. The medical device of claim 11, wherein said block copolymer is a multiarm block copolymer comprising a low Tg midblock selected from polyolefin, polyacrylate and polysiloxane blocks and high Tg endblocks selected from poly(vinyl aromatic) and polymethacrylate blocks, and wherein said additional polymer comprises a low Tg polyolefin block, a low Tg polyacrylate block, a low Tg polysiloxane block, a high Tg poly(vinyl aromatic) block or a high Tg polymethacrylate block.

13. The medical device of claim 1, wherein said layer only partially covers said metallic region.

14. The medical device of claim 1, wherein a therapeutic agent is provided within said polymeric region.

15. The medical device of claim 14, wherein said therapeutic agent is selected from antiproliferative agents, vascular cell growth promoters, antimicrobial agents, analgesic agents, immune-suppression agents, anti-inflammatory agents, antispasmodic agents, alpha blockers, calcium channel blockers, beta agonists, neoplastic agents, cytostatic agents, and combinations thereof.

16. The medical device of claim 1, wherein said medical device is a stent.

17. The medical device of claim 1, wherein said block copolymer is a poly(vinyl aromatic-b-alkene-b-vinyl aromatic) copolymer comprising 20 mol % or more vinyl aromatic monomer.

18. A medical device comprising a polymeric region in the form of a single layer in contact with a metallic region, said polymeric region comprising (a) a block copolymer that comprises (i) a low Tg block selected from polyolefin, polyacrylate and polysiloxane blocks and (ii) a high Tg block selected from poly(vinyl aromatic) and polymethacrylate blocks and (b) an additional polymer that comprises (i) a polymer block selected from a low Tg polyolefin block, a low Tg polyacrylate block, a low Tg polysiloxane block, a high Tg poly(vinyl aromatic) block and a high Tg polymethacrylate block and (ii) an adhesion promoting group selected from halo-silane groups, alkoxy-silane groups, and epoxy groups, and combinations thereof, wherein said additional polymer is covalently bound to said metallic region through said adhesion promoting group, and wherein said medical device is an implantable or insertable medical device.

19. The medical device of claim 18, wherein said additional polymer comprises epoxy groups.

20. The medical device of claim 18, wherein said additional polymer comprises an adhesion promoting group selected from halo-silane groups, alkoxy-silane groups, and combinations thereof.

21. The medical device of claim 18, wherein said block copolymer is a poly(vinyl aromatic-b-alkene-b-vinyl aromatic) copolymer comprising 20 mol % or more vinyl aromatic monomer.

22. The medical device of claim 18, wherein said block copolymer and said additional polymer form an interpenetrating network.

* * * * *